United States Patent [19]

Merritt et al.

[11] 4,281,141

[45] Jul. 28, 1981

[54] 3-(IMIDAZOL-4-YL)-2-PHENYL-PROPANENITRILES

[75] Inventors: Leander Merritt; Richard P. Pioch, both of Indianapolis, Ind.

[73] Assignee: Eli Lilly and Company, Indianapolis, Ind.

[21] Appl. No.: 154,653

[22] Filed: May 30, 1980

[51] Int. Cl.³ .................. C07D 401/06; C07D 233/54
[52] U.S. Cl. ..................................... 548/342; 546/278; 260/465 G; 260/465 K; 424/263; 424/273 R
[58] Field of Search .......................... 548/342; 546/278

[56] References Cited

U.S. PATENT DOCUMENTS

| | | | |
|---|---|---|---|
| 3,190,917 | 6/1965 | Johnson et al. .................. | 548/342 X |
| 4,009,021 | 2/1977 | Yih et al. .......................... | 548/342 X |
| 4,073,921 | 2/1978 | Miller et al. ...................... | 424/273 R |
| 4,115,578 | 9/1978 | Miller et al. ...................... | 546/278 X |
| 4,118,461 | 10/1978 | Miller et al. ...................... | 546/278 X |

OTHER PUBLICATIONS

Sisthane ™ Technical Bulletin of Rohm and Haas Company, 7 pp. (undated).
McDonald et al., J. Org. Chem., 35, (1970), pp. 1250–1254.

*Primary Examiner*—Joseph Paul Brust
*Attorney, Agent, or Firm*—Joseph A. Jones; Arthur R. Whale

[57] ABSTRACT

3-(Imidazol-4-yl)-2-phenylpropanenitriles are useful for control of powdery mildew of cultivated plants.

11 Claims, No Drawings

3-(IMIDAZOL-4-YL)-2-PHENYLPROPANENITRILES

BACKGROUND OF THE INVENTION

1. Field of the Invention

This invention pertains to organic chemistry, and especially to agricultural chemistry. It provides novel compounds which are useful for control of powdery mildew of plants.

2. State of the Art

U.S. Pat. No. 4,073,921, of Miller et al., describes an extensive group of alkanenitriles which are said to be useful as fungicides for the control of plant diseases. Miller describes compounds having an alkane chain of up to twelve carbon atoms, and his compounds have an imidazol-1-yl group at the end of the alkane chain opposite the nitrile group.

SUMMARY OF THE INVENTION

This invention provides a series of 3-(imidazol-4-yl)-2-phenylpropanenitriles of the formula

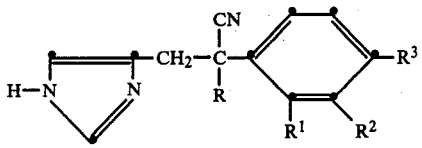

wherein
R is $C_1$–$C_4$ alkyl, 2-pyridyl, phenyl or phenyl mono(3- or 4-)substituted with methyl, bromo, chloro, fluoro or trifluoromethyl;
$R^1$ is hydrogen, chloro, bromo or fluoro;
$R^2$ is hydrogen, methyl, bromo, chloro, fluoro or trifluoromethyl;
$R^3$ is hydrogen, methyl, bromo, chloro, fluoro or trifluoromethyl;
provided that one or both of $R^2$ and $R^3$ is hydrogen; and that $R^1$ is an atom other than hydrogen only when $R^3$ is chloro, bromo or fluoro;
or a non-phytotoxic acid addition salt thereof.

DESCRIPTION OF THE PREFERRED EMBODIMENTS

In the above general formula, the term "$C_1$–$C_4$ alkyl" includes the groups methyl, ethyl, propyl, isopropyl, butyl, s-butyl, i-butyl, and t-butyl.

Certain classes of the compounds of this invention constitute preferred embodiments of the invention. For example, the following groups of compounds include such preferred embodiments. It will be understood that the various classes below may be combined to define further preferred groups of compounds.

Compounds wherein:
(1) R is phenyl;
(2) $R^1$ is hydrogen;
(3) either $R^2$ or $R^3$ is bromo, chloro, methyl or trifluoromethyl;
(4) $R^2$ is hydrogen;
(5) the compound is an acid addition salt;
(6) $R^2$ or $R^3$ is methyl;
(7) R is phenyl or substituted phenyl.

It will be understood that the imidazole group of the compounds may be in either of the two possible tautomeric forms, as follows:

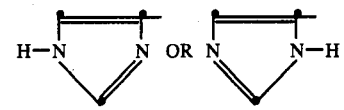

While it is believed that the above general formula clearly explains the nature of the compounds of this invention, a group of representative compounds will be mentioned to assure that the reader readily understands the invention.

3-(imidazol-4-yl)-2-(i-butyl)-2-(3-chlorophenyl)-propanenitrile
3-(imidazol-4-yl)-2-(4-bromophenyl)-2-phenyl-propanenitrile
3-(imidazol-4-yl)-2-(2,4-difluorophenyl)-2-propyl-propanenitrile
3-(imidazol-4-yl)-2-(3-methylphenyl)-2-(3-trifluoromethylphenyl)propanenitrile
3-(imidazol-4-yl)-2-(4-bromophenyl)-2-(4-methylphenyl)propanenitrile
3-(imidazol-4-yl)-2-(2,4-dichlorophenyl)-2-methyl-propanenitrile
3-(imidazol-4-yl)-2-(4-fluorophenyl)-2-(4-trifluoromethylphenyl)propanenitrile
3-(imidazol-4-yl)-2-(t-butyl)-2-(3-fluorophenyl)-propanenitrile
3-(imidazol-4-yl)-2-(4-chlorophenyl)-2-(3-fluorophenyl)propanenitrile
3-(imidazol-4-yl)-2-(2,4-dibromophenyl)-2-ethyl-propanenitrile
3-(imidazol-4-yl)-2-isopropyl-2-(3-methylphenyl)-propanenitrile
3-(imidazol-4-yl)-2-(3-chlorophenyl)-2-(4-trifluoromethylphenyl)propanenitrile
3-(imidazol-4-yl)-2-(3-bromophenyl)-2-(s-butyl)-propanenitrile
3-(imidazol-4-yl)-2-(2-pyridyl)-2-(3-trifluoromethylphenyl)propanenitrile
3-(imidazol-4-yl)-2-(2,4-dibromophenyl)-2-(2-pyridyl)-propanenitrile The compounds are used either in the free base form, or in the form of non-phytotoxic acid addition salts. It will be understood that the acid addition salts referred to here are those which are not significantly more phytotoxic than are the compounds in the free base form. The acid addition salts used here are those which are commonly used in the agricultural chemical and pharmaceutical industries, including the hydrohalides, especially hydrochloride and hydrobromide, the sulfonates, such as the toluenesulfonate and the methanesulfonate, the phosphorus-containing salts such as those formed with phosphoric acid and orthophosphoric acid, the salts of relatively strong organic acids such as those formed by maleic acid, oxalic acid and acetic acid, and other typical acid addition salts such as the nitrate, the sulfate, and the like.

The compounds of this invention are accessible by either of two convenient synthesis methods. All of the compounds are made by the reaction of a 4-halomethylimidazole, wherein halo is chloro or bromo, with a phenylacetonitrile having the desired R through $R^3$ substituents. The reaction is carried out in the presence of a strong base in an inert organic solvent.

The reactants used in this process are known and may be synthesized by any ordinarily skilled organic chemist. The halomethylimidazole is used most conveniently in the form of an acid addition salt, especially a hydrohalide salt.

The strong bases used in the process are chosen from the commonly used reagents such as the alkali metal hydrides, the alkyllithiums, especially butyllithium, the alkali metal alkoxides, and the alkali metal amides. The term "alkali metal" is used here to refer to sodium, potassium and lithium, and the alkoxy groups referred to are those containing from 1 to 4 carbon atoms in each case. The preferred strong base is sodium hydride.

The reaction is carried out in an inert organic solvent, of which the amides, especially dimethylformamide and dimethylacetamide, are preferred. Other solvents may be used as well, such as the ethers, including especially diethyl ether and tetrahydrofuran, and the aromatics, such as benzene, toluene and the xylenes.

The reactions are carried out at moderate temperatures in the range of from about 0° C. to about 100° C., preferably from about the ambient temperature to about 80° C. The reaction times are usually in the range of a few hours; or, in general, from about 15 minutes to about 24 hours.

The reaction mechanism is believed to be as follows. The base first forms the carbanion of the phenylacetonitrile. Accordingly, the first step is to mix the phenylacetonitrile and the base. The halomethylimidazole is then added, in the acid addition salt form as explained above, and the carbanion first removes the salt-forming moiety. The halomethylimidazole then reacts with the carbanion to form the compounds of this invention.

Accordingly, the reaction calls for at least two moles of the phenylacetonitrile and two moles of the base per mole of halomethylimidazole salt, if complete reaction of the halomethylimidazole is to be obtained. Of course, less than two moles may be used if it is unimportant to obtain complete reaction. Excess amounts greater than two moles may be used if desired but have not been found to be necessary. For example, excess amounts above two moles in the range of from 5% to 50% or even more may be used if desired.

The product is isolated by evaporating the solvent, preferably under vacuum, and dissolving the residue in dilute acid. The solution is washed with ether and then made basic. Extraction with ether removes the product in the free base form. It may be converted to a salt, if desired, by contacting it with a dilute acid as discussed above. The product is obtained in a solid form by simply evaporating the solvent in which it is dissolved.

When the product is formed as a salt, it may be converted to the free base, should it be desired to do so, by contacting the salt with a relatively strong base, especially with an aqueous alkali metal hydroxide.

The compounds of this invention, except for those wherein R is 2-pyridyl, are also made by the reaction with formamide of a pentanenitrile of the formula

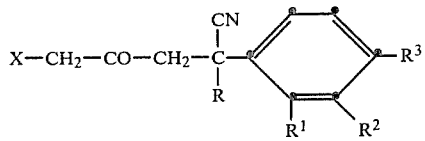

wherein the groups R through $R^3$ are as described above, except that R may not represent 2-pyridyl, and X is chloro or bromo.

The pentanenitriles described above are prepared by reacting a pentenenitrile of the formula

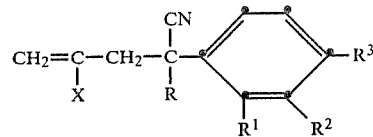

with an oxidizing agent at elevated temperature in the presence of a free radical inhibitor, and the pentenenitriles are prepared by reacting a phenylacetonitrile having the R through $R^3$ substituents of the pentanenitrile with a 2,3-dihalopropene.

In the first step, a 2,3-dihalopropene of the formula

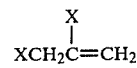

is reacted with a phenylacetonitrile of the formula

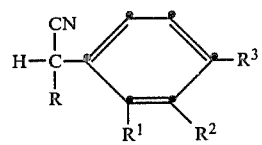

wherein the substituents are as defined above in the definition of the pentanenitriles. The reaction is carried out in the presence of a strong base, as defined above, in an inert organic solvent, such as an ether, including diethyl ether and tetrahydrofuran, an amide such as dimethylformamide, dimethylacetamide or N-methyl-2-pyrrolidone, or an aromatic such as benzene, toluene and the xylenes. The preferred strong base is sodium hydride, and the preferred solvent is dimethylformamide. The base is first reacted with the phenylacetonitrile, and the dihalopropene is then reacted with the resulting carbanion. The reaction temperature is from about 0° C. to about 100° C., preferably from about the ambient temperature to about 75° C. The reaction is complete in from about 15 minutes to about 24 hours, preferably from about 1 to about 4 hours. Equimolar amounts of the reactants and the base are used, and no excess reactant is necessary, but the discussion about excess reactants which was given above also applies to this reaction step.

The pentenenitrile so produced is isolated readily by filtering insoluble inorganic from the reaction mixture and evaporating down to remove the solvent. The intermediate product is used without purification, other than simple water-washing to remove any residue of the base or hydrohalide.

The pentenenitriles are oxidized with an oxidizing agent to form the pentanenitriles. The preferred oxidizing agent is 3-chloroperbenzoic acid; the best oxidizing agents, in general, are organic "per" acids, such as peracetic acid and perbenzoic acid.

It is necessary to use a radical inhibitor in the reaction mixture. A preferred inhibitor is bis-(3-t-butyl-4-hydroxy-5-methylphenyl) sulfide. Other radical inhibitors are also used, including such known compounds as 2,6-bis(t-butyl)-4-methylphenol, 4,4'-butylidenebis(6-t-butyl-3-methylphenol), and dilauryl 3,3'-thiodipropionate.

Only a catalytic amount of the radical inhibitor is needed in the reaction mixture. An excess amount of the oxidizing agent is preferably used in the reaction, such as about 20–50% excess, or even a very large excess, such as 10×. The excess amount which should be used, of course, depends on the relative economics of the oxidizing agent and the pentenenitrile.

The oxidation is preferably carried out in a halogenated hydrocarbon, such as chloroform, dichloroethane and the like, at temperatures in the range from about 50° C. to about 100° C.

While the present invention does not depend on the reaction mechanism, it is believed that the pentanenitriles are formed in two steps. The pentenenitrile is first converted to a 4,5-epoxy-4-halopentanenitrile, which then rearranges to the desired product. See McDonald and Steppel, J. Org. Chem. 35, 1250–54 (1970).

The pentanenitrile is isolated by reducing the remaining oxidizing agent left at the end of the process, and then washing the reaction mixture with a mild base such as dilute aqueous sodium bicarbonate solution. The washed organic layer is then evaporated to dryness and the residue, containing the intermediate product, is dissolved in fresh solvent and filtered to obtain a solution of the intermediate pentanenitrile.

The pentanenitrile is reacted with formamide, either neat or in an inert organic solvent. It is preferred not to use a solvent other than the formamide itself. At least two moles of formamide are needed per mole of pentanenitrile. Excess amounts of formamide may be used as desired, and it is preferred to use enough formamide to make a stirrable reaction mixture. For example, from about 5 to about 25 moles of formamide are preferred. The preferred reaction temperature is the reflux temperature of the reaction mixture in neat formamide, most preferably about 200° C. A temperature range from about 150° C. to about 200° C. is effective, however.

Reaction times in the range of a few hours are preferred, preferably from about ½ hour to about 6 hours; reaction times from about 15 minutes to about 24 hours are used in various instances, as may be convenient.

The product is isolated from the reaction mixture by evaporating the solvent and any excess formamide which may remain, under vacuum, and partitioning the residue between water and an organic solvent such as diethyl ether. The organic layer is then washed with additional portions of water, and the organic layer, containing the product in the free base form, is evaporated to dryness, or the product is converted to the desired salt, depending on the form in which the product is desired.

The following preparative examples are provided to assure that the method of obtaining the compounds of this invention is understood, and that the reader can obtain any desired compound.

EXAMPLE 1

3-(imidazol-4-yl)-2-(3-chlorophenyl)-2-phenyl-propanenitrile

A 9.39 g. portion of 2-(3-chlorophenyl)-2-phenylacetonitrile and 2.04 g. of 50% sodium hydride in mineral oil were combined in 25 ml. of dimethylformamide and stirred for 45 minutes. To the mixture was added 3.06 g. of 4-chloromethylimidazole hydrochloride, dissolved in 25 ml. of dimethylformamide. The reaction mixture was then heated to 60° C., and stirred at that temperature for 1 hour 40 minutes, after which the mixture was allowed to cool to ambient temperature and was stirred for an additional 22 hours. The solvent was then evaporated from the reaction mixture under vacuum, and the residue was dissolved in a mixture of diethyl ether and 1 N hydrochloric acid. The aqueous layer was separated, made basic with 5 N sodium hydroxide, and extracted with diethyl ether. The ether layer was dried over magnesium sulfate, and evaporated to dryness to obtain 5.6 g. of the compound named in the heading, as the free base.

A 3.1 g. portion of the free base was dissolved in ethanol and treated with ethanolic hydrogen chloride to convert it to the hydrochloride salt, which was crystallized from isopropyl alcohol/diethyl ether in a yield of 3.44 g., m.p. 145.5°–149.5° C.

EXAMPLE 2

3-(imidazol-4-yl)-2-(4-bromophenyl)-2-phenyl-propanenitrile

A 10.0 g. portion of 2-(4-bromophenyl)-2-phenylacetonitrile was mixed with 1.76 g. of 50% sodium hydride in 20 ml. of dimethylformamide, and 2.81 g. of 4-chloromethylimidazole hydrochloride in 20 ml. of dimethylformamide was added. The reaction mixture was then stirred at 100° C. for 5 hours, and at ambient temperature for 16 hours. The reaction mixture was worked up as described in Example 1 to obtain 6.1 g. of the free base of the compound named in the heading above. The compound was converted to the maleate salt by contact with maleic acid, and the salt was crystallized from diethyl ether/acetone to obtain 7.80 g. of product, m.p. 121°–124° C.

EXAMPLE 3

3-(imidazol-4-yl)-2-phenyl-2-(2-pyridyl)-propanenitrile

A 19.42 g. portion of 2-(2-pyridyl)-2-phenylacetonitrile was stirred with 4.8 g. of 50% sodium hydride in 50 ml. of dimethylformamide, and reacted with 7.65 g. of 4-chloromethylimidazole hydrochloride in 25 ml. of dimethylformamide as described in Example 1. The mixture was stirred at 80°–90° C. for 1 hour, the solvent was removed by evaporation under vacuum, and wthe residue was worked up as described in Example 1 to obtain 11.87 g. of the free base named in the heading above, m.p. 111°–115° C. dec. The product was triturated twice with portions of diethyl ether, and was dissolved in chloroform. The solution was extracted with water and dried over sodium sulfate. Evaporation of the solvent under vacuum gave 11.84 g. of purified free base, m.p. 111°–115° C.

A 5.4 g. portion of the purified free base was converted to the hydrochloride salt, which was crystallized from ethyl acetate and dried under vacuum at 100° C. to give 5.85 g. of product, m.p. 184°–186° C.

EXAMPLE 4

3-(imidazol-4-yl)-2,2-diphenylpropanenitrile

A 5.80 g. portion of diphenylacetonitrile and 1.5 g. of 50% sodium hydride were reacted for 30 minutes in 20 ml. of dimethylformamide, and 2.29 g. of 4-chloromethylimidazole hydrochloride in 20 ml. of dimethylformamide was added. The reaction mixture was stirred at ambient temperature for about 15 minutes, the solvent was evaporated from the mixture under vacuum, and the residue was worked up as described in Example 1 to obtain 3.0 g. of the desired product as the free base, which was identified by 60 mHz nuclear magnetic resonance analysis in CDCl$_3$, showing the following characteristic peaks: δ9.05 (broad m, 1H); 7.32 (m, 11H); 6.60 (s, 1H); 3.68 (s, 2H).

EXAMPLE 5

3-(imidazol-4-yl)-2-(2,4-dichlorophenyl)-2-phenylpropanenitrile

According to the scheme of Example 1, 2.04 g. of 50% sodium hydride, 11.64 g. of 2-(2,4-dichlorophenyl)-2-phenylacetonitrile, and 3.06 g. of 4-chloromethylimidazole hydrochloride were reacted at about 60° C. for 2 hours. The reaction mixture was then allowed to cool to ambient temperature and was stirred for 64 hours. The solvent was then evaporated and the reaction mixture was worked up as described in Example 1. The product was converted to the hydrochloride salt, and crystallized from ethyl acetate/diethyl ether to obtain 6.86 g. of the hydrochloride salt of the product named in the heading above, m.p. 215°–218° C.

EXAMPLE 6

3-(imidazol-4-yl)-2,2-bis(4-chlorophenyl)-propanenitrile

As described in Example 1, 7.26 g. of 2,2-bis(4-chlorophenyl)acetonitrile, 1.33 g. of 50% sodium hydride and 2.12 g. of 4-chloromethylimidazole hydrochloride were reacted in 50 ml. of dimethylformamide. The mixture was stirred for 2 hours at 60° C. and then 21 hours at ambient temperature. The solvent was then evaporated off under vacuum and the reaction mixture was worked up as described in Example 1 to obtain 5.2 g. of the free base named above, which was converted to the maleate salt and crystallized from acetone/diethyl ether to obtain 5.73 g. of the maleate salt of the product named above, m.p. 151.5°–153° C.

EXAMPLE 7

3-(imidazol-4-yl)-2-(4-chlorophenyl)-2-phenylpropanenitrile

As described in Example 1, 2.04 g. of 50% sodium hydride, 10.12 g. of 2-(4-chlorophenyl)-2-phenylacetonitrile, and 3.06 g. of 4-chloromethylimidazole hydrochloride were reacted in 50 ml. of dimethylformamide. The reaction mixture was stirred for one hour at 60° C. and then for 20 hours at ambient temperature. Evaporation of the solvent and work up as described in Example 1 produced 5.3 g. of the product named above, which was converted to the maleate salt and crystallized from acetone/diethyl ether to obtain 6.29 g. of the maleate salt of the desired product, m.p. 135°–136° C.

EXAMPLE 8

3-(imidazol-4-yl)-2-methyl-2-phenylpropanenitrile

As described in Example 1, 5.82 g. of 2-phenylpropanenitrile, 2.04 g. of 50% sodium hydride, and 3.06 g. of 4-chloromethylimidazole hydrochloride were reacted in 40 ml. of dimethylformamide. The mixture was stirred for 5 hours at 100° C., and for 16 hours at ambient temperature. The solvent was then evaporated away under vacuum, and the residue was worked up as described in Example 1 to obtain 0.4 g. of crude free base. The product was purified by preparative thin layer chromatography on silica gel with ethyl acetate as the eluant. The purified product was converted to 0.11 g. of the hydrochloride salt of the desired product, m.p. 187°–189° C.

EXAMPLE 9

3-(imidazol-4-yl)-2-butyl-2-phenylpropanenitrile

A 7.62 g. portion of 2-butyl-2-phenylacetonitrile, 2.11 g. of 50% sodium hydride and 3.06 g. of 4-chloromethylimidazole hydrochloride were reacted as described in Example 1, and the reaction mixture was stirred for 18 hours at 95° C. The solvent was then evaporated and the reaction mixture was worked up as described in Example 1 to obtain 0.72 g. of crude product.

The crude product above was purified by high pressure liquid chromatography over silica gel, with ethanol/ethyl acetate as the eluant, to obtain 0.30 g. of purified free base, which was reacted with oxalic acid to obtain 0.20 g. of the oxalate salt of the product named above, m.p. 134°–136° C., after crystallization from ethanol/ethyl acetate/acetone.

EXAMPLE 10

3-(imidazol-4-yl)-2-(4-fluorophenyl)-2-phenylpropanenitrile

As described in Example 1, 3.0 g. of 2-(4-fluorophenyl)-2-phenylacetonitrile, 1.36 g. of 50% sodium hydride and 2.17 g. of 4-chloromethylimidazole hydrochloride were mixed, and the reaction mixture was stirred at 60° C. for 3 hours and then at ambient temperature for 65 hours. The reaction mixture was then worked up as described in Example 1 to obtain 2.60 g. of the free base of the product named above, which was identified by 60 mHz nuclear magnetic resonance analysis in CDCl$_3$: δ10.65 (broad m, 1H); 7.37 (m, 8H); 6.88 (d, 2H, J=9 Hz); 6.65 (s, 1H), 3.70 (s, 2H).

The free base was converted to the maleate salt and crystallized from ethanol/diethyl ether to obtain 3.74 g. of the salt, m.p. 122°–125° C.

EXAMPLE 11

3-(imidazol-4-yl)-2-phenyl-2-(4-trifluoromethylphenyl)-propanenitrile

A 3.84 g. portion of 2-phenyl-2-(4-trifluoromethylphenyl)acetonitrile was reacted with 1.42 g. of 50% sodium hydride and 2.25 g. of 4-chloromethylimidazole hydrochloride in 50 ml. of dimethylformamide, as described in Example 1. The mixture was stirred for 2 hours at 60° C., and for 20 hours at ambient temperature. The reaction mixture was then worked up as described in Example 1 to obtain 3.6 g. of the desired product as the free base, a sample of which was analyzed as follows.

Theoretical: C, 66.86; H, 4.13; N, 12.31; Found: C, 66.61; H, 4.43; N, 12.05

EXAMPLE 12

3-(imidazol-4-yl)-2-(3-chlorophenyl)-2-(4-chlorophenyl)propanenitrile

A 7.26 g. portion of 3,4'-dichlorodiphenylacetonitrile was reacted with 1.33 g. of 50% sodium hydride and 2.12 g. of 4-chloromethylimidazole hydrochloride, as described in Example 1, and the mixture was stirred at 60° C. for 2½ hours, and at ambient temperature for 67 hours. The reaction mixture was then worked up as described in Example 1 to obtain 4.2 g. of the free base of the product named in the heading above, which was converted to the hydrochloride salt and crystallized twice from ethanol/ethyl acetate to obtain 4.46 g. of the hydrochloride salt of the desired product, m.p. 138°–140° C.

EXAMPLE 13

3-(imidazol-4-yl)-2-(4-methylphenyl)-2-phenyl-propanenitrile

A 50.7 g. portion of 2-(4-methylphenyl)-2-phenylacetonitrile was dissolved in 200 ml. of dimethylformamide, and 11.74 g. of 50% sodium hydride was added. The mixture was stirred for about 1 hour, and was then warmed to 50° C. To the mixture was added a solution of 18.72 g. of 4-chloromethylimidazole hydrochloride in 200 ml. of dimethylformamide. After the addition, the mixture was stirred for three hours at 50° C. and was then stirred for 15 hours at ambient temperature. The reaction mixture was worked up as described in Example 1 to obtain 19.5 g. of the free base of the product named in the heading above, which was identified by 60 mHz nuclear magnetic resonance analysis in $CDCl_3$, showing the following characteristic peaks: $\delta 9.87$ (broad m, 1H); 7.40 (m, 10H); 6.68 (s, 1H); 3.73 (s, 2H); 2.32 (s, 3H).

The unreacted nitrile from the reaction mixture was recovered and reacted again to obtain 11.7 g. of additional free base. These portions of product were combined and reacted with hydrochloric acid. The salt was crystallized from methanol/ethyl acetate to obtain 28.9 g. of the hydrochloride salt of the product named above, m.p. 165°–181° C. It was dissolved in methanol and crystallized from methyl ethyl ketone to obtain 20 g. of ketone-wet product, m.p. 194°–197° C. The salt was crystallized again from methyl ethyl ketone to obtain 15.4 g. of purified salt, m.p. 195°–200° C.

The MEK liquors were combined and converted to the free base, which was purified by high pressure liquid chromatography. The purified base, amounting to 6.0 g., was dissolved in ethanol and converted to the hydrochloride salt to give 6.6 g. of additional desired product, in the hydrochloride form, m.p. 188°–193° C. after crystallization from ethyl acetate. All of the crops of product were combined and recrystallized from ethanol/ethyl acetate to obtain 22 g. of product, m.p. 192.5°–195.5° C.

The following preparation illustrates the synthesis of the intermediate pentenenitriles which are used in the alternate synthesis of compounds of this invention.

PREPARATION 1

2-butyl-4-chloro-2-phenyl-4-pentenenitrile

A 7.62 g. portion of 2-phenylhexanenitrile and 2.11 g. of 50% sodium hydride were combined in 30 ml. of dry dimethylformamide, and the mixture was stirred for 1.5 hours at 50°–55° C. The mixture was then cooled to 20° C. and 4.88 g. of 2,3-dichloro-1-propene was added dropwise, followed by an additional 10 ml. of dry dimethylformamide. The reaction mixture warmed spontaneously to about 35° C., and it was warmed to 55° C. after the addition and was stirred at that temperature for 1.5 hours. The mixture was then allowed to cool to ambient temperature and was stirred for 64 hours. It was then filtered to remove insoluble inorganics, and the solids were washed with ethyl acetate. The filtrate was evaporated under vacuum to an oil, which was dissolved in diethyl ether and was washed with water. The residue was taken up in ethanol and evaporated to dryness under vacuum to obtain 10.85 g. of the crude product named in the heading above. The product was identified by 60 mHz nuclear magnetic resonance analysis in $CDDl_3$: $\delta 7.37$ (m, 5H); 5.25 (d, 1H, J=2 Hz); 5.08 (d, 1H, J=2 Hz); 2.93 (s, 2H); 1.97 (dt, 2H); 1.25 (m, 4H); 0.83 (t, 3H).

PREPARATION 2

4-chloro-2,2-diphenyl-4-pentenenitrile

A 40.3 g. portion of sodium amide was suspended in 400 ml. of dry toluene at 70° C. and 199.6 g. of diphenylacetonitrile, dissolved in 600 ml. of hot dry toluene, was added dropwise. The mixture was stirred at 70°–100° C. for 4 hours, and an additional 500 ml. of dry toluene and 100 ml. of dimethylformamide were added. The mixture was stirred for 27 hours more. The slurry was cooled to 10° C., and 114.6 g. of 2,3-dichloropropene was added. The mixture was warmed to ambient temperature and stirred for 40 hours, and was then stirred at 90°–100° C. for one hour. The mixture was then cooled to ambient temperature, diluted with a large amount of diethyl ether, washed with water and dried over magnesium sulfate. The solution was evaporated to give 265 g. of crude liquid product.

The following preparations demonstrate the synthesis of the pentanenitriles which are immediate intermediates for the synthesis of compounds of the present invention.

PREPARATION 3

2-butyl-5-chloro-2-phenyl-4-oxopentanenitrile

The intermediate product made in Preparation 1 was combined with 0.17 g. of bis(3-t-butyl-4-hydroxy-5-methylphenyl) sulfide in 100 ml. of 1,2-dichloroethane, and the mixture was heated to the reflux temperature. To it was added 12.31 g. of 3-chloroperbenzoic acid in 110 ml. of warm 1,2-dichloroethane, dropwise. The mixture was stirred at the reflux temperature for 40 hours, and an additional 6.16 g. of 3-chloroperbenzoic acid and 0.20 g. of the sulfide dissolved in 50 ml. of 1,2-dichloroethane were added, and the reflux was continued for a total of 69 hours. The reaction mixture was then cooled, and to it was added, dropwise, 250 ml. of 10% sodium sulfite solution, followed by 9 g. of sodium bicarbonate dissolved in 100 ml. of water. The organic layer was separated and washed with water, and was then evaporated to dryness under vacuum. The residue was taken up in ethanol and evaporated to dryness under vacuum, and that step was repeated twice more. The residue was then taken up in 1,2-dichloroethane and filtered, and the filtrate was evaporated to dryness to obtain 12.35 g. of crude product, which was identified by 60 mHz nuclear magnetic resonance analysis in $CDCl_3$, showing the following characteristic peaks: $\delta 7.38$ (m, 5H); 3.88 (s, 2H); 3.32 (s, 2H); 1.97 (dt, 2H); 1.25 (m, 4H); 0.85 (t, 3H).

PREPARATION 4

5-chloro-4-oxo-2,2-diphenylpentanenitrile

A 265 g. portion of 4-chloro-2,2-diphenylpentenenitrile and 3.84 g. of bis(3-t-butyl-4-hydroxy-5-methylphenyl) sulfide were dissolved in 1 liter of 1,2-dichloroethane and heated to the reflux temperature, about 75°–80° C. To the mixture was added dropwise a solution of 276.9 g. of 3-chloroperbenzoic acid dissolved in 2.5 liters of 1,2-dichloroethane. The resulting solution was heated for 24 hours, and was then cooled to ambient temperature. Sodium sulfite solution was added until starch-iodide paper showed a negative test for peracid. The reaction mixture was then made basic by the addition of 135 g. of sodium bicarbonate in saturated aqueous solution, and the organic layer was then separated, washed with water and dried over sodium sulfate. The solvent was then evaporated away under vacuum to obtain 294.5 g. of crude product, which was crystallized from ethanol to obtain 194.3 g. of the product named in the heading, m.p. 102°–104° C.

The following two examples show syntheses of compounds of this invention from the intermediate pentanenitriles.

EXAMPLE 14

3-(imidazol-4-yl)-2,2-diphenylpropanenitrile

A 5.68 g. portion of the product of Preparation 4 above was dissolved in 20 ml. of formamide, and was stirred at the reflux temperature for 2 hours. The mixture was evaporated to a gum under vacuum, and the gum was shaken with a mixture of diethyl ether and sodium hydroxide solution. The organic layer was extracted with dilute hydrochloric acid, and the acid layer was extracted with diethyl ether, and made basic with dilute sodium hydroxide solution. The basic solution was extracted with diethyl ether and evaporated under vacuum to obtain 3.2 g. of the free base named above, in crude form. The free base was reacted with 1.43 g. of maleic acid to obtain 2.58 g. of the maleate salt of the product named above, m.p. 156.5°–158.5° C., after it had been crystallized twice from acetone.

EXAMPLE 15

3-(imidazol-4-yl)-2-butyl-2-phenylpropanenitrile

The product of Preparation 3 above was added to 50 ml. of formamide and the mixture was stirred at the reflux temperature for 3.75 hours. The excess formamide was then removed under vacuum, and the residue was partitioned in a diethyl ether/water mixture. The organic layer was separated and washed with water until the wash liquid was clear. The ether solution was then extracted with 100 ml. of 1 N hydrochloric acid, and was washed with water. The two aqueous extracts were combined, and were extracted with diethyl ether until the extract was clear. The aqueous layer was then made basic with 5 N sodium hydroxide solution, and was extracted again with diethyl ether. The ether extract was dried over sodium sulfate, filtered, and evaporated to dryness to give 3.7 g. of crude product. Mass spectroscopic analysis showed a molecular ion of weight 253. The material was converted to the oxalate salt by dissolving it in a large volume of diethyl ether with oxalic acid. The crude product amounted to 4.4 g. of insoluble solid, which was recrystallized from acetone/ethyl acetate to obtain 3.8 g. of the oxalate salt of the product named above, m.p. 143°–150° C. The salt was dissolved in methanol, decolorized with activated charcoal and recrystallized from isopropanol/ethyl acetate to obtain 2.44 g. of purified oxalate salt, m.p. 150°–153° C. dec.

The compounds of this invention have been shown by in vivo tests to protect plants from the adverse effects of powdery mildew. The following examples illustrate the tests employed and the results produced by representative compounds.

Each compound was formulated for testing by dissolving or suspending about 3.5 weight percent of it in 1:1 acetone:ethanol containing about 10 g./100 ml. of a non-ionic surfactant. The mixture was then dispersed in deionized water in a quantity such that the water dispersion contained the various compound concentrations indicated below. Concentrations are measured in parts per million by weight.

When the compound was applied to the foliage of the test plant, the dispersion was sprayed on the plant with an air atomizer, using enough dispersion to wet the leaves and stems thoroughly. Other methods of application were used as described in the specific methods below.

Untreated, infected controls and untreated normal controls were included in each test period. The results are reported on a 1–5 rating scale where 1 indicates severe, uncontrolled disease and 5 indicates complete control of the disease. An empty space in the table indicates that the indicated compound was not tested at the indicated rate. Compounds are identified by the example number used above.

The following specific test methods were used.

TEST 1

Powdery mildew of bean

The host plants were 10-day-old bean seedlings. Aqueous dispersions containing test compounds at concentrations indicated in the table below were sprayed on the foliage of the beans and allowed to dry, and the plants were placed in the greenhouse and inoculated by storing them under other bean plants which were heavily infected with powdery mildew (*Erysiphe polygoni*). After about 10 days, the plants were observed and the results recorded.

TEST 2

The host plants were 6-day-old wheat seedlings, growing in 6-cm. round plastic pots. The plants were sprayed with dispersions of the test compounds as described above, and were infected with *Erysiphe graminis tritici* by dusting them with conidia from infected plants. The plants were stored in the greenhouse for about 7 days and were then observed.

TEST 3

Wheat seedlings were used in a test carried out as described under Test 2, except that the compounds were applied by pouring 10 ml. of a dispersion on the soil surface of each pot. The amount of compound in the dispersion was adjusted to provide the application rates named in Table I below.

TABLE 1

| Example | Test | Rate | Result |
|---|---|---|---|
| 1, HCl | 1 | 400 ppm | 4 |
|  | 2 | 400 | 3 |
|  | 3 | 12.3 kg/ha | 3 |
| 2, maleate | 1 | 400 ppm | 4 |
|  | 1 | 400 | 4 |
|  | 1 | 400 | 5 |
|  | 1 | 100 | 1 |
|  | 1 | 25 | 1 |
|  | 2 | 400 | 4 |
|  | 2 | 400 | 4 |
|  | 2 | 100 | 4 |
|  | 2 | 25 | 3 |
|  | 3 | 12.3 kg/ha | 1 |
| 3, HCl | 1 | 400 ppm | 4 |
|  | 1 | 400 | 3 |
|  | 2 | 400 | 1 |
|  | 2 | 400 | 4 |
|  | 2 | 100 | 1 |
|  | 2 | 25 | 1 |

TABLE 1-continued

| Example | Test | Rate | Result |
|---|---|---|---|
| | 3 | 12.3 kg/ha | 4 |
| | 3 | 12.3 | 4 |
| | 3 | 3.4 | 4 |
| | 3 | 0.78 | 1 |
| 4, maleate | 1 | 400 ppm | 4 |
| | 1 | 400 | 4 |
| | 1 | 400 | 4 |
| | 1 | 100 | 4 |
| | 1 | 25 | 4 |
| | 2 | 400 | 3 |
| | 2 | 400 | 5 |
| | 2 | 100 | 1 |
| | 2 | 25 | 1 |
| | 3 | 12.3 kg/ha | 5 |
| | 3 | 12.3 | 4 |
| | 3 | 3.4 | 5 |
| | 3 | 0.78 | 3 |
| 5, HCl | 1 | 400 ppm | 4 |
| | 2 | 400 | 3 |
| | 2 | 400 | 4 |
| | 2 | 100 | 1 |
| | 2 | 25 | 1 |
| | 3 | 12.3 kg/ha | 1 |
| 6, maleate | 1 | 400 ppm | 5 |
| | 1 | 400 | 5 |
| | 1 | 400 | 5 |
| | 1 | 100 | 4 |
| | 1 | 25 | 2 |
| | 2 | 400 | 5 |
| | 2 | 400 | 4 |
| | 2 | 100 | 4 |
| | 2 | 100 | 4 |
| | 2 | 25 | 3 |
| | 2 | 25 | 4 |
| | 2 | 6 | 4 |
| | 3 | 12.3 kg/ha | 1 |
| 7, maleate | 1 | 400 ppm | 5 |
| | 1 | 400 | 5 |
| | 1 | 400 | 5 |
| | 1 | 100 | 4 |
| | 1 | 25 | 2 |
| | 2 | 400 | 4 |
| | 2 | 400 | 5 |
| | 2 | 100 | 4 |
| | 2 | 100 | 5 |
| | 2 | 25 | 3 |
| | 2 | 25 | 4 |
| | 2 | 6 | 4 |
| | 3 | 12.3 kg/ha | 3 |
| 8, HCl | 2 | 400 ppm | 4 |
| | 2 | 100 | 3 |
| | 2 | 25 | 1 |
| | 2 | 6 | 1 |
| 9, oxalate | 1 | 400 ppm | 5 |
| | 1 | 400 | 5 |
| | 1 | 400 | 5 |
| | 1 | 100 | 3 |
| | 1 | 25 | 1 |
| | 2 | 400 | 3 |
| | 2 | 400 | 5 |
| | 2 | 400 | 4 |
| | 2 | 100 | 4 |
| | 2 | 100 | 1 |
| | 2 | 25 | 3 |
| | 2 | 25 | 1 |
| | 2 | 6 | 1 |
| 9, oxalate | 3 | 12.3 kg/ha | 5 |
| | 3 | 12.3 | 5 |
| | 3 | 12.3 | 5 |
| | 3 | 3.4 | 4 |
| | 3 | 3.4 | 4 |
| | 3 | 0.78 | 1 |
| | 3 | 0.78 | 3 |
| | 3 | 0.22 | 1 |
| 10, maleate | 1 | 400 ppm | 5 |
| | 1 | 400 | 5 |
| | 1 | 400 | 4 |
| | 1 | 100 | 3 |
| | 1 | 25 | 1 |
| | 2 | 400 | 1 |
| | 3 | 12.3 kg/ha | 1 |
| 11, base | 1 | 400 ppm | 1 |
| | 2 | 400 | 4 |
| | 2 | 400 | 5 |
| | 2 | 100 | 4 |
| | 2 | 100 | 5 |
| | 2 | 25 | 4 |
| | 2 | 25 | 4 |
| | 2 | 6 | 3 |
| | 3 | 12.3 kg/ha | 4 |
| | 3 | 12.3 | 4 |
| | 3 | 3.4 | 3 |
| | 3 | 0.78 | 1 |
| 12, HCl | 1 | 400 ppm | 1 |
| | 2 | 400 | 4 |
| | 2 | 400 | 4 |
| | 2 | 100 | 4 |
| | 2 | 25 | 1 |
| | 3 | 12.3 kg/ha | 1 |
| 13, base | 2 | 400 ppm | 4 |
| | 2 | 400 | 4 |
| | 2 | 100 | 4 |
| | 2 | 25 | 3 |
| | 3 | 12.3 kg/ha | 1 |
| | 3 | 12.3 | 4 |
| | 3 | 3.4 | 1 |
| | 3 | 0.78 | 1 |
| 13, HCl | 1 | 400 ppm | 5 |
| | 2 | 400 | 5 |
| | 2 | 400 | 5 |
| | 2 | 100 | 3 |
| | 2 | 100 | 5 |
| | 2 | 25 | 3 |
| | 2 | 25 | 4 |
| | 2 | 6 | 3 |
| | 3 | 12.3 kg/ha | 4 |
| | 3 | 12.3 | 4 |
| | 3 | 3.4 | 1 |
| | 3 | 0.78 | 1 |

TEST 4

A test was carried out on direct-seeded bush summer squash, growing in rows on a sandy soil in a semi-tropical climate.

When the test began, the squash plants were about five weeks old. Each test plot consisted of one row of squash plants, 6.1 meters long. The squash suffered from a natural infestation of powdery mildew (Erysiphe species); the disease incidence was about 5% at the time the compound was applied.

The compound of Example 13, as the hydrochloride salt, was dispersed in water for application. Applications were made by a tractor-mounted sprayer moving at about 3 kilometers per hour. The spray solution was applied through atomizing nozzles at 2.8 kg./sq. cm., at a volume rate of 748 liters per hectare. The concentration of the compound in the spray solutions was adjusted to give the application rates shown in the table below.

Four applications of the test compound were made, on the first, seventh, fourteenth and twenty-first days of the experiment. The test plots were observed on the schedule shown in the table below, and assessments of injury to the crop and incidence of disease were made. Injury and disease are measured in percent injury or percent disease control, relative to untreated controls.

TABLE II

| | Day 5-7 | | Day 26 | |
|---|---|---|---|---|
| Appl'n Rate | Injury | Disease Control | Injury | Disease Control |
| 0.28 kg/ha | 0% | 90% | 0% | 100% |

TABLE II-continued

| | Day 5-7 | | Day 26 | |
|---|---|---|---|---|
| Appl'n Rate | Injury | Disease Control | Injury | Disease Control |
| 0.56 | 0 | 92 | 0 | 100 |
| 1.12 | 10 | 94 | 0 | 100 |

TEST 5

The compound of Example 7, as the maleate salt, was applied to zinnia infected with powdery mildew (Erysiphe species) in field tests carried out on a clay loam soil in a midwestern area. When the test began, the plants were about six weeks old. Applications of the test compound were made on the first day of the experiment, and again after two and four weeks of the experiment. The zinnia plants were grown in rows, and each test plot included 4.6 meters of a single row.

The test compound was formulated as an emulsifiable concentrate containing about 25% of the compound by weight in a solvent-surfactant mixture including non-ionic and anionic surfactants, and aromatic and ether solvents.

Applications of the compound were made as aqueous dispersions, using a small powered sprayer. The application volume was about 935 liters per hectare in all experiments, and the spray was directed to the lower 8-12 centimeters of the plants. The following results were observed.

TABLE III

| | Disease Control | |
|---|---|---|
| Appl'n Rate | 5 weeks | 7 weeks |
| 25 q./ha | 70% | 36% |
| 50 | 82 | 36 |
| 100 | 67 | 45 |

TEST 6

This test was carried out on winter wheat in the midwestern United States. The wheat had been planted in October, and the test compound was applied May 28, at a time when the wheat showed a trace of powdery mildew on the lower leaves. The wheat was in the heading stage.

Each test plot was an area 1.5×3 meters, and the test compound was applied in a volume of 2 liters of spray solution per plot. A back-pack sprayer was used. The compound, which was the compound of Example 13 in the hydrochloride form, was supplied as a 50% water-soluble powder. The compound was applied twice, on the first and fifth days of the experiment, and the test plots were observed on the eleventh day of the experiment to determine control of powdery mildew.

TABLE IV

| Appl'n Rate | Disease Control |
|---|---|
| 0.28 kg/ha | 0% |
| 0.56 | 0 |
| 1.12 | 35 |

TEST 7

Another test on wheat was carried out, substantially according to the scheme of Test 6. In this experiment, the compound was applied on the first, eighth and thirteenth days of the experiment, and the test plots were observed for crop injury and control of powdery mildew (*Erysiphe graminis*) on the twenty-fifth day of the experiment. The test compound caused no crop injury. The test compound, the hydrochloride of the compound of Example 13, gave 60% control of powdery mildew at 0.28 kg/ha, 68% control at 0.56, and 75% control at 1.12 kg/ha application rates.

TEST 8

This test was carried out on direct-seeded zinnias in the midwestern United States. The zinnias were about two months old when the test began, and the test compound was applied at the start of the experiment, and again at approximately the 2-week, 3-week and 5-week points in the experiment. The test plots, each of which consisted of one 3-meter row, were observed at the sixth week of the experiment.

The disease affecting the zinnias was powdery mildew (*Erysiphe cichoracearum*).

The test compound, that of Example 13 in the hydrochloride form, was formulated as a 20% water-soluble powder. Solutions of the compound were applied with a back-pack sprayer, at a volume of 1 liter per 3 test plots.

Application of the compound at a concentration of 150 ppm. by weight and also at 300 ppm. by weight in the solution gave 33% control of powdery mildew. Application at 600 ppm. by weight gave 66% control.

TEST 9

This test was carried out on winter squash in the southwestern United States. The squash plants were about 7 weeks old when the test was established, and applications of the test compound were made at the start of the experiment, and at the fifth, ninth and fourteenth days thereafter.

The test compound was the hydrochloride salt of the compound of Example 13, formulated as a 20% water-soluble powder.

Each test plot was one 6.1-meter row of plants. The compound was dissolved in water, and the solutions were applied at a volume rate of 748 liters per hectare, using a tractor-mounted sprayer.

The test plants were observed for crop injury and disease incidence of powdery mildew (*Erysiphe cichoracearum*) on the days listed in the table below.

None of the treatments caused any crop injury.

TABLE V

| | Disease Incidence | | | |
|---|---|---|---|---|
| Appl'n Rate | Day 5 | Day 9 | Day 14 | Day 20 |
| 0.14 kg/ha | 28% | 37% | 85% | 87% |
| 0.28 | 25 | 12 | 65 | 63 |
| 0.56 | 37 | 28 | 38 | 70 |
| 1.12 | 8 | 32 | 30 | 43 |
| Control | 47 | 56 | 91 | 96 |

TEST 10

This test was substantially like Test 9, except that the experiment was carried out in the semi-tropical United States, and the solutions of the test compound were applied at the volume rate of 935 liters per hectare. The plants were about 3 weeks old when the experiment began, and the test compound was applied on the first day of the experiment and each week thereafter.

The compound was applied at only one rate, 0.56 kg/ha.

The test compound caused no injury to the crop.

Ratings of percent control of powdery mildew were made on day 14 of the experiment, and on day 34. At each date, the test compound gave essentially 100% control of an extremely severe infestation of powdery mildew.

The number of fruit on the plants was counted on day 23 of the experiment, and on day 35 of the experiment. The first count showed that the test plots had 20% more fruit than the control plots, and the second count showed 77% more fruit than the control plots.

The data reported above show that the compounds of this invention are useful for the protection of plants from the adverse effects of powdery mildew. As agricultural chemists will understand, use of the compounds of this invention does not necessarily kill all, or even any, of the phytopathogens. As the data show, however, application of a fungicidally-effective amount of a compound reduces the adverse effects of the disease, even though only a part, or even none, of the phytopathogen population may be killed by the compound. The term "fungicidally effective amount" is used here to describe an amount which is adequate to reduce the adverse effects of the phytopathogen.

The compounds of this invention are useful against the various plant diseases of the powdery mildew group. The diseases are primarily caused by organisms of the Erysiphe genus, including *Erysiphe polygoni*, causative of powdery mildew of bean, *Erysiphe graminis tritici*, causative of powdery mildew of wheat, and *Erysiphe cichoracearum*, causative of powdery mildew of cucurbits and zinnia.

The invention is preferably used to protect wheat from *Erysiphe graminis tritici*. The compounds with which the invention is preferably carried out are 3-(imidazol-4-yl)-2-(4-methylphenyl)-2-phenylpropanenitrile, 3-(imidazol-4-yl)-2-(4-chlorophenyl)-2-phenylpropanenitrile, 3-(imidazol-4-yl)-2,2-bis(4-chlorophenyl)propanenitrile, 3-(imidazol-4-yl)-2-phenyl-2-(4-trifluoromethylphenyl)propanenitrile, and 3-(imidazol-4-yl)-2-(4-bromophenyl)-2-phenylpropanenitrile.

The compounds are applied either to the foliage of plants or to the soil in which they grow, preferably to the foliage of the plants to be protected. It is preferable to begin application of the compounds before a serious infestation of powdery mildew starts, but the compounds can effectively be applied to infested plants. It is preferable to apply the compounds every 7 to 14 days through the period in which powdery mildew is a danger.

The methods of formulating the compounds and preparing dispersions of the formulations, and the methods of applying dispersions of the compounds, are entirely conventional in the plant protection art. Some explanation of the methods of application will be given merely to assure that those skilled in the art can readily carry out the invention. The amount of the compound to apply may be described either in terms of the amount of compound applied per unit area of soil, or in terms of the concentration of the compound in the dispersion. Soil applications of the compounds, and applications to low-growing plants such as cucurbits, are usually measured in terms of amount of compound per unit area. Compound application rates in the range of from about 0.1 to about 10 kg/ha are used. Application rates higher or lower than the named range will be useful at times, depending upon the severity of the infection, the weather and the characteristics of the specific compound in use. Preferred application rates are in the general range of from about 0.5 to about 5 kg/ha.

When the compound is to be applied to the foliage of bushy plants, such as beans, it is more usual to measure the application rate in terms of the concentration of the compound in the dispersion. Concentrations in the range from about 10 ppm. to about 1000 ppm. by weight are used; preferred concentrations are usually from about 100 to about 600 ppm. Again, concentrations higher or lower than the named ranges may be needed at times, depending on the conditions existing in the crop.

The dispersions in which the compounds are applied are most often aqueous suspensions or emulsions prepared from concentrated formulations of the compounds. Such water-soluble, water-suspendable or emulsifiable formulations are either solids usually known as wettable powders or soluble powders, or liquids usually known as emulsifiable concentrates or aqueous suspensions. Wettable powders, which may be compacted to form wettable granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenol.

Since the compounds of this invention form water-soluble salts, they may be used as water-soluble powders. Such powders are easily formulated simply by dispersing the acid addition salt of one of the compounds of this invention in a water-soluble solid such as an inorganic salt, or a water-dispersible soluble extender such as starch, a polyvinyl alcohol, and the like. Small amounts of surfactants such as those mentioned above are also added, in some cases, to assist in dispersing and dissolving the formulation. Water-soluble powders are formulated at concentrations in the range from about 10% to about 90% by weight.

Emulsifiable concentrates of the compounds comprise a convenient concentration of the compound, such as from about 10% to about 50% by weight of liquid, dissolved in an inert carrier which is a mixture of water-immiscible organic solvent and emulsifiers. Useful organic solvents include the aromatics, especially the xylenes, and the petroleum fractions, especially the high-boiling napthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants discussed above.

Aqueous suspensions comprise suspensions of water-insoluble compounds of this invention, usually the free base forms, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts, may also be added, to increase the density of the aqueous vehicle. It is often most effective to grind and mix the compound at the same time by preparing the aqueous mixture, and homogenizing it in an implement such as a sand mill, ball mill, or piston-type homogenizer.

Concentrated aqueous solutions containing in the range of from about 5% to about 25% of water-soluble compounds of this invention may also be prepared and used as concentrated formulations.

The following formulae are exemplary of typical formulations of the compound, which are referred to here by their example numbers. The formulae are in percent by weight.

| Wettable Powders | | |
|---|---|---|
| I. | | |
| Example 2, free base | | 10% |
| sodium lauryl sulfate | | 6 |
| sulfonated lignin | | 3 |
| attapulgite clay | | 81 |
| II. | | |
| Example 6, free base | | 50% |
| alkyl sulfonate | | 5 |
| polyoxyethylene ether | | 1 |
| colloidal silica | | 3 |
| kaolin clay | | 41 |
| III. | | |
| Example 7, free base | | 90% |
| alkyl sulfate | | 1 |
| sodium lignin sulfonate | | 0.5 |
| colloidal silica | | 8.5 |
| IV. | | |
| Example 10, free base | | 75% |
| calcium alkyl sulfonate | | 3 |
| naphthalene sulfonate | | 2 |
| colloidal silica | | 1 |
| montmorillonite clay | | 19 |
| Soluble Powders | | |
| I. | | |
| Example 13, hydrochloride | | 50% |
| Potassium chloride | | 50 |
| II. | | |
| Example 8, hydrochloride | | 10% |
| Starch powder | | 90 |
| III. | | |
| Example 1, hydrochloride | | 90% |
| Sodium alkyl sulfate | | 1 |
| Potassium chloride | | 9 |
| Emulsifiable Concentrates | | |
| I. | | |
| Example 7, maleate | | 25% |
| 2-methoxyethanol | | 20 |
| metal sulfonate/polyoxyethylene ether blend | | 10 |
| xylene | | 45 |
| II. | | |
| Example 5, free base | | 10% |
| metal sulfonate/polyoxyethylene ether blend | | 7 |
| 2-methoxyethanol | | 20 |
| xylene | | 63 |
| III. | | |
| Example 12, free base | | 50% |
| metal sulfonate/polyoxyether blend | | 10 |
| 2-ethoxyethanol | | 30 |
| xylene | | 10 |
| Solution Concentrates | | |
| I. | | |
| Example 7, hydrochloride | | 5% |
| Water | | 95 |
| II. | | |
| Example 4, hydrochloride | | 25% |
| Water | | 75 |

We claim:

1. A compound of the formula

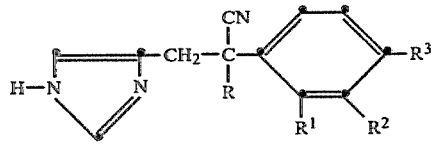

wherein
R is $C_1$–$C_4$ alkyl, 2-pyridyl, phenyl or phenyl mono (3- or 4-) substituted with methyl, bromo, chloro, fluoro or trifluoromethyl;
$R^1$ is hydrogen, chloro, bromo or fluoro;
$R^2$ is hydrogen, methyl, bromo, chloro, fluoro or trifluoromethyl;
$R^3$ is hydrogen, methyl, bromo, chloro, fluoro or trifluoromethyl;
provided that one or both of $R^2$ and $R^3$ is hydrogen; and that $R^1$ is an atom other than hydrogen only when $R^3$ is chloro, bromo or fluoro;
or a non-phytotoxic acid addition salt thereof.

2. A compound of claim 1 wherein R is phenyl or substituted phenyl.

3. A compound of claim 1 wherein R is phenyl.

4. A compound of claim 3 wherein $R^1$ is hydrogen.

5. A compound of claim 4 wherein either $R^2$ or $R^3$ is bromo, chloro, methyl or trifluoromethyl.

6. A compound of claim 5 wherein $R^2$ is hydrogen.

7. The compound of claim 1 which is 3-(imidazol-4-yl)-2-(4-methylphenyl)-2-phenylpropanenitrile or a non-phytotoxic acid addition salt thereof.

8. The compound of claim 1 which is 3-(imidazol-4-yl)-2-(4-chlorophenyl)-2-phenylpropanenitrile or a non-phytotoxic acid addition salt thereof.

9. The compound of claim 1 which is 3-(imidazol-4-yl)-2,2-bis(4-chlorophenyl)propanenitrile or a non-phytotoxic acid addition salt thereof.

10. The compound of claim 1 which is 3-(imidazol-4-yl)-2-phenyl-2-(4-trifluoromethylphenyl)propanenitrile or a non-phytotoxic acid addition salt thereof.

11. The compound of claim 1 which is 3-(imidazol-4-yl)-2-(4-bromophenyl)-2-phenylpropanenitrile or a non-phytotoxic acid addition salt thereof.

* * * * *